United States Patent [19]

Terwilliger

[11] Patent Number: 4,524,623

[45] Date of Patent: Jun. 25, 1985

[54] TRANSDUCER DRIVE ASSEMBLY

[75] Inventor: Richard A. Terwilliger, Los Gatos, Calif.

[73] Assignee: Diasonics, Inc., Milpitas, Calif.

[21] Appl. No.: 583,990

[22] Filed: Feb. 27, 1984

[51] Int. Cl.³ ............................................. G01N 29/00
[52] U.S. Cl. ...................................... 73/633; 74/22 R; 74/26; 128/660
[58] Field of Search .................. 73/618, 619, 633, 634, 73/640; 128/660; 74/22 R, 25, 26

[56] References Cited

U.S. PATENT DOCUMENTS

| | | | |
|---|---|---|---|
| 3,752,255 | 8/1973 | Hill et al. | 73/633 |
| 4,120,291 | 10/1978 | Paton et al. | 73/618 |
| 4,215,585 | 8/1980 | Kunic et al. | 74/25 |
| 4,377,088 | 3/1983 | Evert | 73/618 |
| 4,462,255 | 7/1984 | Guess et al. | 73/633 |

*Primary Examiner*—Howard A. Birmiel

*Attorney, Agent, or Firm*—Blakely, Sokoloff, Taylor & Zafman

[57] ABSTRACT

A transducer drive assembly is disclosed having particular application for use in medical diagnostic imaging systems. The drive assembly includes a rotor coupled to drive means for rotation about its longitudinal axis. The rotor is formed such that it includes an integrally formed contact plate which extends upwardly from a generally flat rotor face at a given angle. A transducer is carried in a cradle which is mounted for pivotal movement, and includes a lower base portion having a generally cylindrical cross section. The lower base portion of the cradle is disposed such that it is maintained in physical contact with the rotor contact plate at all times. The rotation of the rotor applies force to the lower base of the cradle resulting in the oscillation of the cradle about the pivot points. The transducer is thereby oscillated back and forth about the pivot points in a uniform and continuous movement so long as the rotor continues to rotate.

12 Claims, 11 Drawing Figures

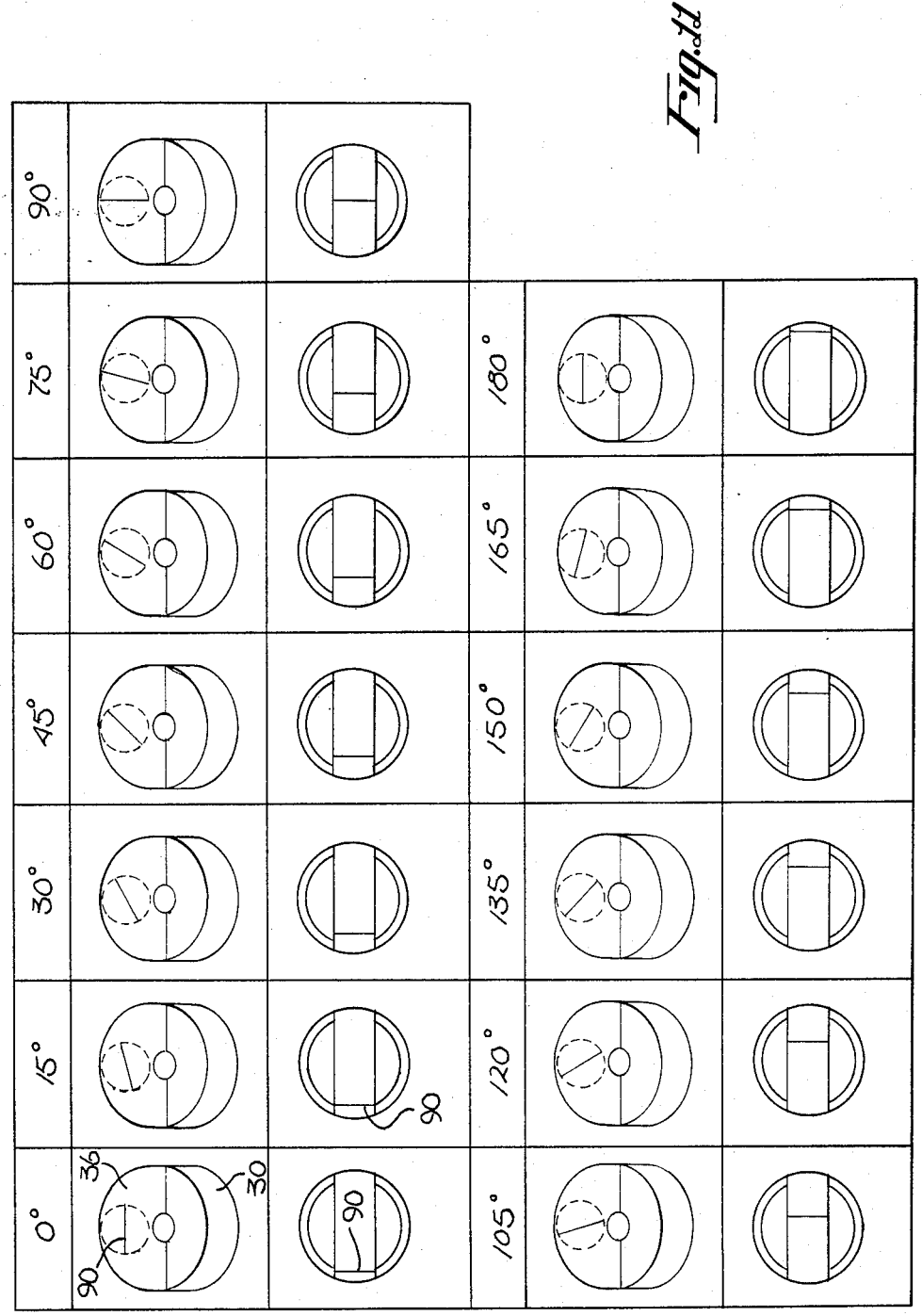

TRANSDUCER DRIVE ASSEMBLY

BACKGROUND OF THE INVENTION

1. Field of the Invention:

The present invention relates to the field of ultrasonic scanners, and in particular, to drive assemblies which permit an ultrasonic transducer to scan a portion of the body.

2. Art Background

Within the past decade, the use of ultrasound for medical diagnostic purposes has found wide application. Unlike prior methods such as x-ray, surgery or the like, ultrasonic energy as used in medical diagnostics is considered safe. Ultrasonic scanning is frequently used to obtain pictorial cross-sections of the body, measuring th peformance of the heart and blood flow and for identifying tumors, cysts, and other abnormalities. In addition, ultrasonic scanning has particular application to the examination of pregnant women and infants. In the field of obstetrics, ultrasonic scanning has almost completely supplanted older methods of visualizing the uterus.

A variety of ultrasonic scanning systems have been developed which include various mechanisms in order to oscillate an ultrasonic transducer in order to pemit the scanning of a section of the body. See for example, U.S. Pat. Nos. 4,215,585, 4,130,021 and 4,120,291. However, prior art transducer drive assemblies typically include pin and slot coupling arrangements for oscillating a transducer about a given axis. The pin in slot mechanical coupling invariably produces shimmey problems which reduce the accuracy of the scanning systems' ability to position an ultrasonic transducer.

As will be described, the present invention provides an ultrasonic transducer drive assembly which virtually eliminates mechanical play and inaccuracies in the drive mechanism. The present invention provides a direct, cost efficient, and highly reliable transducer drive assembly.

DESCRIPTION OF THE DRAWINGS

FIG. 11 is a diagram illustrating rotor rotation vs. contact line position on the cradle.

SUMMARY OF THE INVENTION

A transducer drive assembly is disclosed having particular application for use in medical diagnostic imaging systems. The drive assembly includes a rotor coupled to drive means for rotation about its longitudinal axis. The rotor is formed such that it includes an integrally formed contact plate which extends upwardly from a generally flat rotor face at a given angle. A transducer is carried in a cradle which is mounted for pivotal movement, and includes a lower base portion having a generally cylindrical cross section. The lower base portion of the cradle is disposed such that it is maintained in physical contact with the rotor contact plate at all times. The rotation of the rotor applies force to the lower base of the cradle resulting in the oscillation of the cradle about the pivot points. The transducer is thereby oscillated back and forth about the pivot points in a uniform and continuous movement so long as the rotor continues to rotate.

DETAILED DESCRIPTION OF THE INVENTION

A transducer drive assembly is disclosed having particular application for use in medical diagnostic imaging systems. In the following description, numerous details are set forth such as specific frequencies, transducer types, tolerances, thicknesses, materials, etc. in order to provide a thorough understanding of the present invention. However, it will be apparent to one skilled in the art that the invention may be practiced without these specific details. In other instances, well known components, structures and the like have not been described in detail in order not to obscure the present invention unnecessarily.

Figures 1, 2:
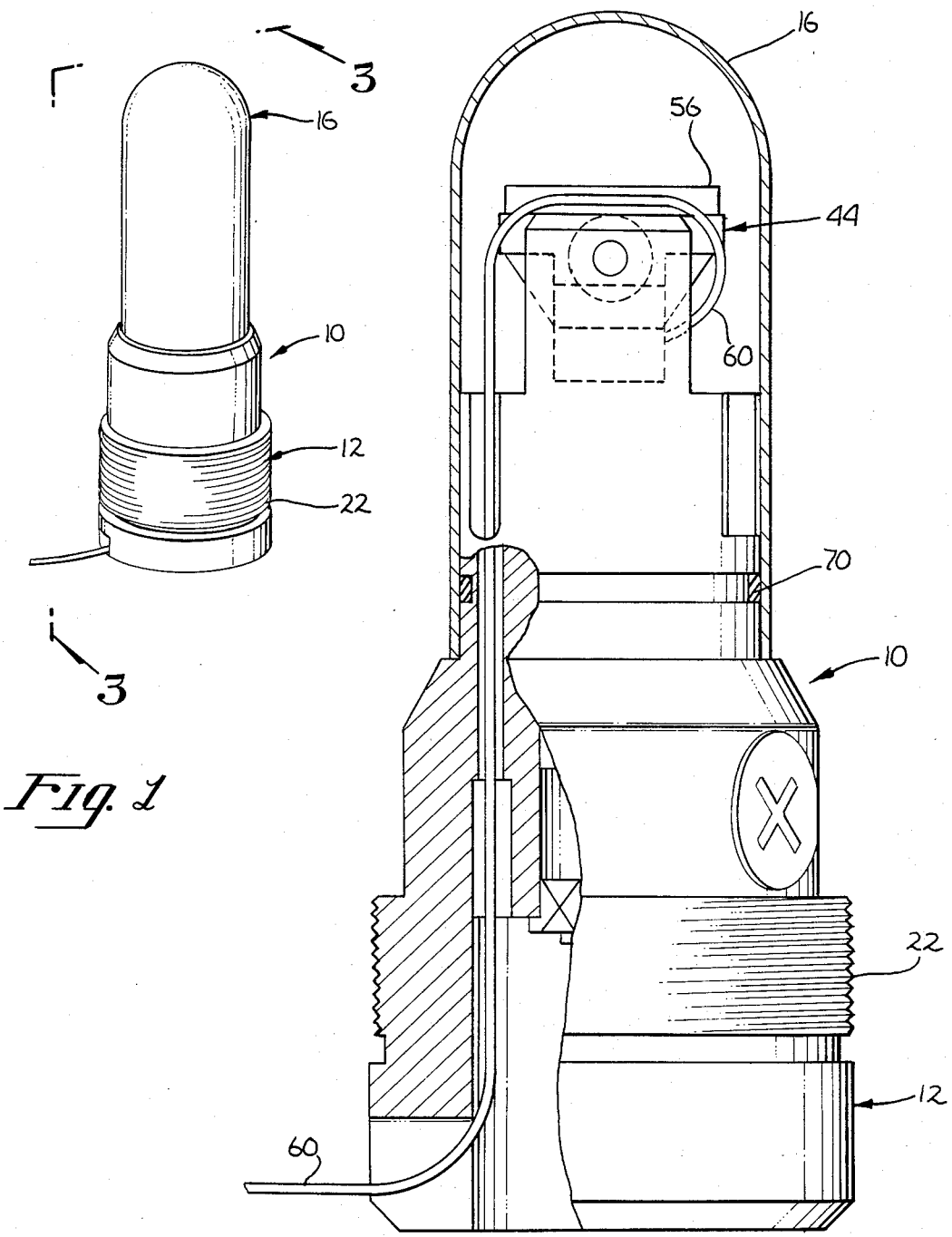
FIG. 1 is a perspective view illustrating the housing of the present invention.
FIG. 2 is a partial cut-away side view of the present invention shown in FIG. 1.

Referring to FIG. 1, the present invention's transducer drive assembly is disposed in a drive assembly housing 10, which includes a base 12 and an ultrasonic transparent cap 16. As illustrated, base 12 includes threads 22 which permit the housing incorporating the present invention's drive assembly to be mechanically coupled to ultrasonic scanning units which include appropriate motor assemblies and electronics.

Figure 3:
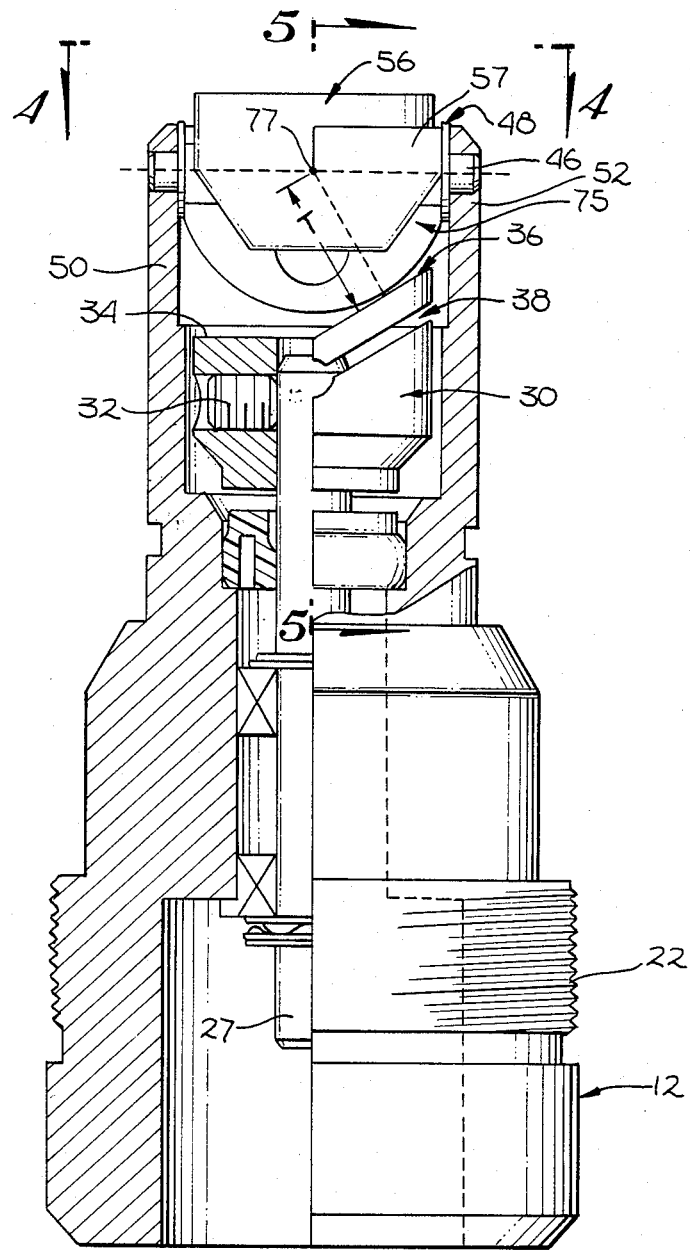
FIG. 3 is a partial cross-section of the present invention wherein the ultrasonic transparnt cap has been removed in order to illustrate the transducer drive assembly of the present invention.
Figure 4:
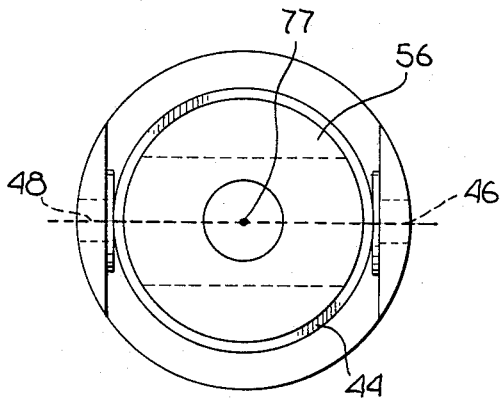
FIG. 4 is a top view illustrating the placement of a transducer in the pivotally mounted cradle of the present invention.
Figure 5:
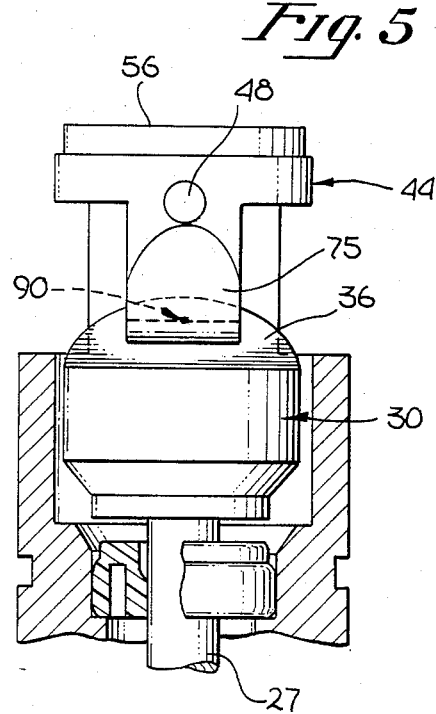
FIG. 5 is a partial cross-section and side view of the present invention illustrating the placement of the rotor when the transducer cradle is in a centered position taken along line 5—5 of FIG. 3.
Figure 6:
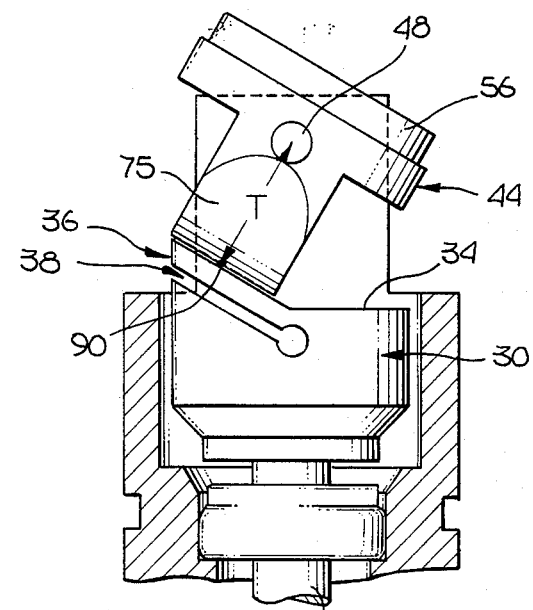
FIG. 6 is a partial cross-section and side view of the present invention illustrating the placement of the rotor when the transducer is rotated fully in one direction.
Figure 7:
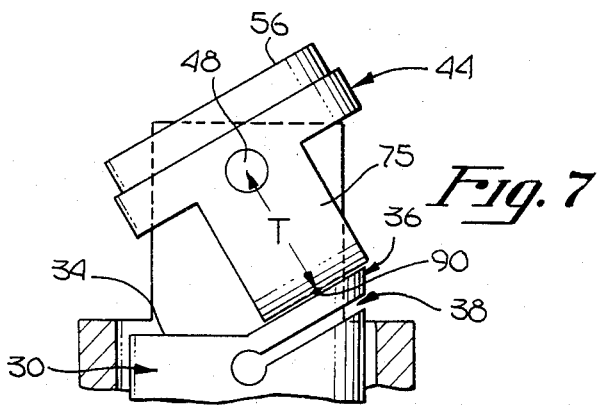
FIG. 7 is a partial cross-section and side view of the drive assembly of the present invention illustrating the placement of the rotor when the transducer is rotated to an opposite position.

Referring to FIGS. 2 and 3, the transducer drive assembly of the present invention includes a motor shaft 27 which is coupled to a motor (not shown) typically located in a hand holdable ultrasonic scanning unit. Motor shaft 27 is coupled through base 12, using appropriate bearings and seals, to a rotor 30. As shown, rotor 30 includes a set screw 32 which is used to mechanically couple rotor 30 to motor shaft 27, such that the rotation of motor shaft 27 is translated into a direct rotation of the rotor 30. As illustrated in FIGS. 3, 5, 6, 7, 8 and 9, rotor 30 is generally cylindrical in shape and includes a generally flat face section 34, and an upwardly extending contact plate 36. Contact plate 36 is integrally formed with the main body of rotor 30, and extends upward in the present embodiment at an angle of approximately 45° relative to the face section 34. Rotor 30 is formed with a slot 38 traversing approximately one-half the circumference of the rotor 30, which is located between the contact plate 36 and the main body of rotor 30, to provide a spring action such that the contact plate 36 may deform in response to forces applied to it, as will be described more fully below. In the presently preferred embodiment, rotor 30 comprises a rigid polymer material, such as "Delrin", nylon, plastic or the like.

As shown in the Figures, a cradle 44 is pivotally supported at pivot points 46 and 48 between forked projections 50 and 52, which extend upward from the main base 12 of housing 10. Cradle 44 carries an ultrasonic transducer 56 which is supported in the cradle by a circumferential band 57 which surrounds transducer 56. Inasmuch as transducer 56 is rigidly coupled to cradle 44, the oscillation of cradle 44 about pivot points 46 and 48 will result in the corresponding movement of transducer 56.

Referring to FIGS. 5, 6, 7, 8 and 10, cradle 44 includes a lower base portion 75 generally having a shape best defined as a segment of a cylinder. In the present embodiment, lower base portion 75 has a substantially cylindrical cross-section, with a width "W" approximately equal to the width of the contact plate 36. It will be appreciated that other widths and dimensions may also have utility depending on the particular application in which the present invention is used. As illustrated, lower base portion 75 is maintained in physical contact with the contact plate 36 of the rotor 30. A central point 77 may be defined as the point wherein an imaginary line extending along the longitudinal axis of rotor 30 intersects the midpoint of the pivotal axis of cradle 44, between pivot points 46 and 48. The distance between the central point 77 and the contact plate 36 may be defined as "T", which corresponds to the radius of curvature of lower base portion 75, and remains constant throughout the 360 degree rotation of rotor 30. Accordingly, as rotor 30 rotates, an imaginary line drawn between the central point 77 and contact plate 36 defines the locus of a cone having an apex at point 77.

Ultrasonic transducer 56 is coupled to well known electronics through a cable 60 for appropriate transmission and reception of ultrasonic signals. As shown in FIG. 2, the ultrasonic transparent cap 16 matingly engages base 12 and is sealed through the use of "O" ring 70, such that ultrasonic coupling fluid may surround the ultrasonic transducer 56 within the ultrasonic transducer cap 20. Ultrasound signals eminating from transducer 56 are then passed with little attenuation to the body under examination.

Figure 8:
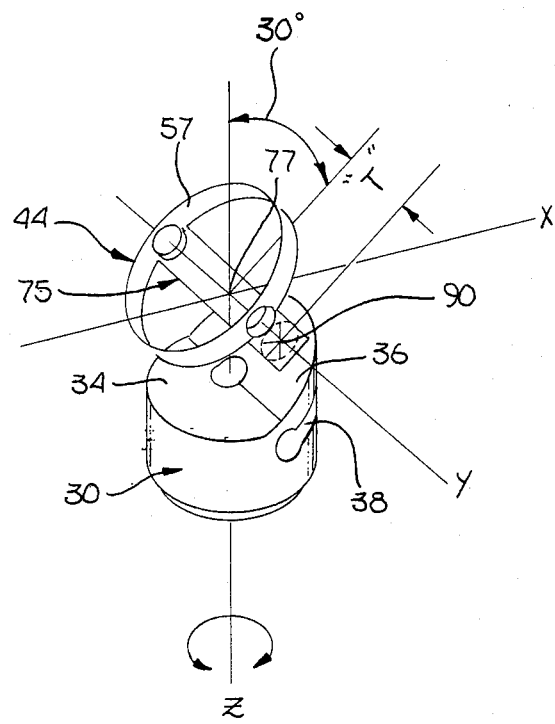
FIG. 8 is a diagramatical illustration of the contact lines between the transducer cradle of the present invention and the rotor.
Figure 9:
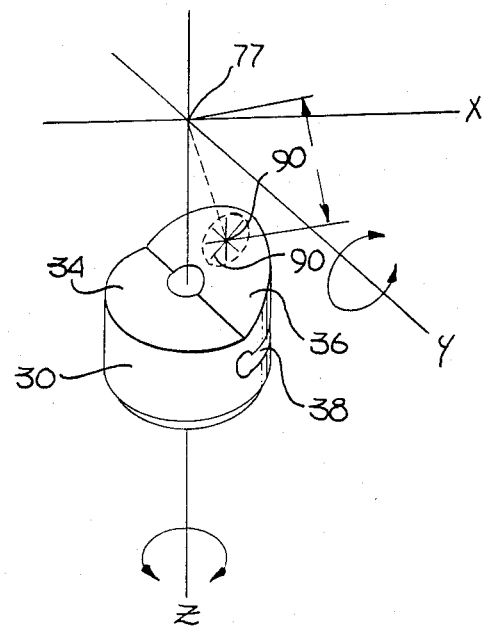
FIG. 9 is an illustration of the rotation of the contact line between the cradle and rotor throughout the 360 degree rotor rotation.
Figure 10:
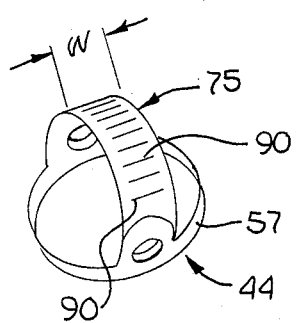
FIG. 10 is an illustration of the contact line position through a 180 degree rotor rotation.

With reference to FIGS. 3 through 11, in operation, motor shaft 27 is rotated by an appropriate motor assembly (not shown) which directly results in the rotation of rotor 30. As will be described, the rotation of rotor 30 in turn results in the application of force to the lower base 75 of the cradle 44, in such a manner that the cradle is forced to oscillate about pivot points 46 and 48. As illustrated in FIGS. 5, 8, 9 and 11, a "contact line" 90 between the lower base portion 75 and the contact plate 36 may be defined as the locus of points on the radius of the lower base portion 75 which physically contact the contact plate 36, as the rotor 30 rotates through 360 degrees. In the present embodiment, this locus of points forms a line on the contact plate 36 for any given position in the rotation of rotor 30. As best shown in FIGS. 8 and 9, as rotor 30 rotates, the contact line 90 also rotates and defines a "contact circle" on the contact plate 36. It will be noted that although contact line 90 defines a circle on the contact plate 36 as the rotor 30 rotates, with respect to lower base portion 75 of cradle 44, the contact line 90 simply appears to move across the lower portion 75 in accordance with the rotational position of rotor 30. The relative movement of the contact points defining the contact line 90, with respect to the contact plate 36 and the lower base portion 75, is illustrated in FIG. 11. As shown, due to the specific geometry of the present invention, the position of the contact line 90 varies as a function of the relative angular increments of the rotation of the rotor 30. The position of contact line 90 disclosed in FIG. 11 is repeated for every 180 degree rotation of the rotor 30.

As previously noted, lower base portion 75 of cradle 44 is disposed such that it is in physical contact with the contact plate 36, thereby defining the contact line 90. In practice, cradle 44 is formed out of a highly polished stainless steel, and rotor 30 is formed from "Delrin", the entire assembly being surrounded by a lubricating coupling fluid contained within the cap 16. Thus, friction between the contact plate 36 and cradle 44 is reduced to a minimum. Slot 38 is designed to act as a semi-loaded leaf spring between the contact plate 36 and the lower base portion 75, to correct for any misalignment between the rotor 36 and the cradle 44. Misalignment between the rotor 36 and the cradle 44 would result in asymmetry between the rotational axis of the rotor 30 and central point 77. Any asymmetry between the rotor's rotational axis and the central point 77 would result in a non-uniform oscillation of the cradle 44 about pivot points 46 and 48. Accordingly, slot 38 insures that the distance "T" remains constant throughout the rotation of the rotor 30.

The above described geometry of the present invention effectively restrains the movement of cradle 44 in the Y and Z axis, but permits rotation about the X axis defined through the pivot points 46 and 48. The maintainance of rotor 30 in contact with the lower base portion 75 which has a cylindrical cross-section in conjunction with the rotation of the rotor 30, thereby forces the cradle to oscillate about pivot points 46 and 48. The magnitude of the cradle oscillation (in degrees) relative to the logitudinal axis of the rotor 30 is a function of the angle of the contact plate 36 with respect to the lower base portion 75. In the presently preferred embodiment, cradle 44 oscillates with a total sweep of 60 degrees relative to the longitudinal axis of rotor 30. However, it will be appreciated, that by selectively altering the angle of the contact plate 36, a total sweep of approximately 0-179 degrees may be obtained.

It has been found that the drive assembly of the present invention virtually eliminates mechanical shimmy. In addition, the use of rotor 30 in combination with the cradle 44 permits the transducer to be accurately oscillated about pivot points 46 and 48 in order to provide detailed ultrasonic images. Although the present invention's drive assembly has been disclosed in relation to the overall structure of housing 10, it will be appreciated that the present invention may be incorporated into a variety of housing designs.

I claim:
1. An improved drive assembly for oscillating an article, comprising:
   a frame;
   a cradle for carrying said article pivotally fastened to said frame at pivot points, said cradle including a lower base section formed generally in the shape of a segment of a cylinder;
   a rotor including a body and an upwardly extending contact plate, said contact plate extending upward from said body at a predetermined angle, such that at least some portion of said contact plate is maintained in physical contact with at least some portion of said lower base section at all times;

drive means coupled to said rotor for rotating said rotor about its longitudinal axis, the rotation of said rotor forcing said cradle to oscillate about said pivot points;

whereby said article is oscillated about said pivot points.

2. The improved drive assembly as defined by claim 1, wherein said rotor is disposed such that its longitudinal axis intersects the mid-point of the axis of rotation of said cradle between said pivot points.

3. The improved drive assembly as defined by claim 2, wherein the points of contact between said lower base portion and said contact plate form a contact line, the position of said contact lines on said lower base portion being a function of the rotational position of said rotor.

4. The improved drive assembly as defined by claim 3, wherein the rotation of said rotor results in said contact line having a locus of points defining a circle on said contact plate once said rotor rotates 360 degrees.

5. The improved drive assembly as defined by claim 4, wherein said rotor includes a generally cylindrical body, and said contact plate extends upwardly from a generally flat face portion of said rotor.

6. The improved drive assembly as defined by claim 5, wherein said article is a transducer.

7. The improved drive assembly as defined by claim 6, wherein said cradle includes a circumferential retaining band surrounding said transducer.

8. The improved drive assembly as defined by claim 7, wherein said rotor includes a slot formed in said rotor below said contact plate such that said contact plate may deform and spring back in response to applied forces, thereby maintaining said rotor and cradle in alignment.

9. The improved drive assembly as defined by claim 8, wherein said slot is formed in said rotor such that it traverses approximately one-half the circumference of said rotor, and is disposed below said contact plate.

10. The improved drive assembly as defined by claim 9, wherein said predetermined angle of said contact plate is 45°.

11. The improved drive assembly as defined by claim 10, wherein said rotor is comprised of a plastic.

12. The improved drive assembly as defined by claim 11, further including an ultrasonic transparent cap enclosing said assembly and containing an ultrasonic coupling fluid.

* * * * *